(12) United States Patent
Gueret

(10) Patent No.: US 7,186,045 B2
(45) Date of Patent: Mar. 6, 2007

(54) DEVICE AND METHOD FOR APPLYING A COSMETIC PRODUCT

(75) Inventor: Jean-Louis H. Gueret, Paris (FR)

(73) Assignee: L'Oreal S.A., Paris (FR)

( * ) Notice: Subject to any disclaimer, the term of this patent is extended or adjusted under 35 U.S.C. 154(b) by 261 days.

(21) Appl. No.: 10/810,644

(22) Filed: Mar. 29, 2004

(65) Prior Publication Data

US 2004/0247373 A1    Dec. 9, 2004

Related U.S. Application Data

(63) Continuation-in-part of application No. 09/779,873, filed on Feb. 8, 2001, now abandoned.

(30) Foreign Application Priority Data

Feb. 16, 2000    (FR) .................................. 00 01902

(51) Int. Cl.
*A45D 33/00*    (2006.01)
*A46B 11/00*    (2006.01)
(52) U.S. Cl. ................. 401/130; 401/126; 401/123
(58) Field of Classification Search ................ 401/123, 401/124, 126, 130, 121; 15/104.93, 104.94
See application file for complete search history.

(56) References Cited

U.S. PATENT DOCUMENTS

| | | |
|---|---|---|
| 4,631,297 A | 12/1986 | Battice et al. |
| 4,806,572 A | 2/1989 | Kellett |
| 5,013,459 A | 5/1991 | Gettings et al. |
| 5,105,993 A | 4/1992 | La Haye et al. |
| 5,154,325 A | 10/1992 | Ryder et al. |

(Continued)

FOREIGN PATENT DOCUMENTS

DE    34 38 186 A1    4/1986

(Continued)

OTHER PUBLICATIONS

The Map to Microbial Control, Byotrol Technical Data Sheet, 2 pages, publication date unknown.

(Continued)

*Primary Examiner*—David J. Walczak
(74) *Attorney, Agent, or Firm*—Finnegan, Henderson, Farabow, Garrett & Dunner, LLP

(57) ABSTRACT

A device for applying a cosmetic product may include a receptacle configured to be closed so as to place the receptacle in at least a substantially sealed condition. The receptacle may include a reservoir configured to contain the cosmetic product, and an applicator for applying the cosmetic product. The applicator may be configured to be contained in the receptacle, and the device may be configured so as to permit loading of the applicator with cosmetic product from the reservoir, wherein the applicator may include a porous structure. The device may be configured such that the receptacle is configured to be unsealed from the at least substantially sealed condition so as to permit the applicator to be used for application of the cosmetic product, and to be returned to the at least substantially sealed condition with the applicator contained in the receptacle. The porous structure may include at least one biocidal agent.

47 Claims, 4 Drawing Sheets

U.S. PATENT DOCUMENTS

| | | | |
|---|---|---|---|
| 5,620,270 | A | 4/1997 | Gueret |
| 5,865,194 | A | 2/1999 | Gueret |
| 5,928,631 | A | 7/1999 | Lucas et al. |
| 6,180,584 | B1 | 1/2001 | Sawan et al. |
| 6,464,418 | B1 * | 10/2002 | Visser et al. .................. 401/34 |

FOREIGN PATENT DOCUMENTS

| | | |
|---|---|---|
| EP | 302 575 | 2/1989 |
| FR | 2 588 835 | 4/1987 |
| JP | 58-180537 | 10/1983 |
| JP | 59-28909 | 2/1984 |
| JP | 02-35964 | 2/1990 |
| JP | 02-116311 | 5/1990 |
| JP | 04-207179 | 7/1992 |
| JP | 8-173237 | 7/1996 |
| JP | 9-220117 | 8/1997 |
| JP | 11-170761 | 6/1999 |
| JP | 11-302381 | 11/1999 |
| WO | WO 02/062142 | 8/2002 |

OTHER PUBLICATIONS

Byotrol *Material Safety Data Sheet*, acc to ISO/DIS 11014, 6 pages, Aug. 15, 2001.

Byotrol Information Page, printed on Feb. 25, 2004, at http://www.byotrol.com/how.htm.

Preliminary Results of Acute Toxicity Testing with Byotrol E4L Concentrate and 2% w/w Solution, printed on Feb. 25, 2004, at http://www.byotrol.com/toxicity.htm.

Byotrol is a biodegradable biocide!, printed on Feb. 25, 2004, at http://www.byotrol.com/bio.htm.

Byotrol LLC was established . . . , printed on Feb. 25, 2004, at http://www.byotrol.com/company.htm.

Biocides, Chemical or Physical agents that kill or inactivate microorganisms, printed on Feb. 25, 2004, at http://www.byotrol.com/glossary.htm.

The Principles Behind Byotrol, 2 pages, printed on Mar. 24, 2004, at http://www.hansonco.net.

Byotrol an Introduction, Mike McNicholas, Byotrol LLC, 19 pages, printed on Mar. 25, 2004, at http://dis-system.com/Byotrol%20_introduction.ppt.

English Language Translation of FR 2 588 835, dated Apr. 24, 1987.

Letter dated Oct. 14, 2002, from Lee Hanson to Walter MacKay, regarding "Byotrol Sample-Broad Band & Long Lasting Efficacy for Foam."

Japanese Official Action dated Mar. 15, 2004 (2 pages).

English-language translation of Japanese Official Action dated Mar. 15, 2004 (1 page).

Partial English-translation of JP 11-302381.

Partial English-translation of JP 11-170761.

\* cited by examiner

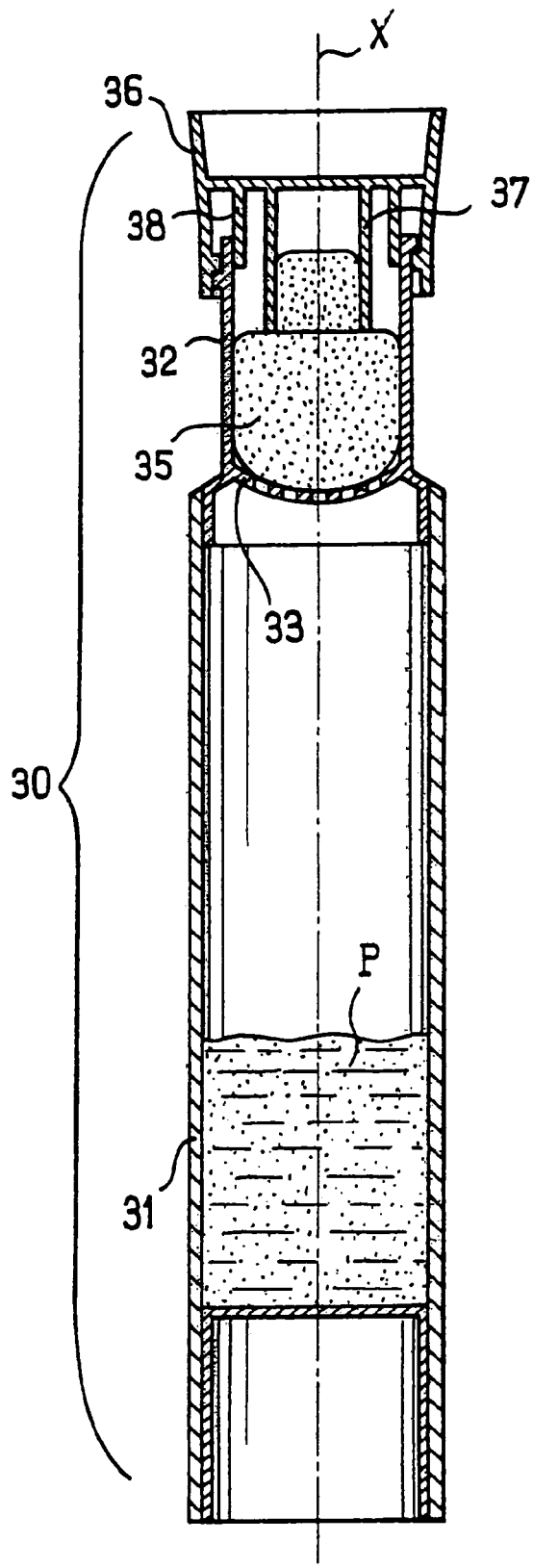
FIG_3
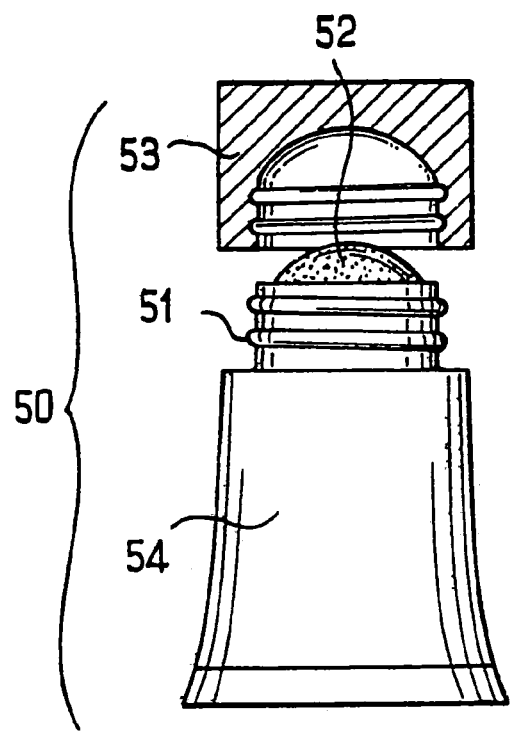
FIG_4

DEVICE AND METHOD FOR APPLYING A COSMETIC PRODUCT

This application is a continuation-in-part (CIP) application of U.S. patent application Ser. No. 09/779,873, filed Feb. 8, 2001 now abandoned.

The present invention relates to a device for applying a cosmetic product. For example, the invention may relate to a packaging and/or applicator device that may include a receptacle configured to be closed in an at least substantially sealed manner, and an applicator including a porous structure, such as, for example, a foam element having open cells, for applying the substance.

There exists a need to avoid including preservatives in certain substances, for example, when the substance is a cosmetic product for sensitive areas, such as, for example, the face.

In the following description, certain aspects and embodiments will become evident. It should be understood that the invention, in its broadest sense, could be practiced without having one or more features of these aspects and embodiments. It should be understood that these aspects and embodiments are merely exemplary.

In one aspect, as embodied and broadly described herein, the invention includes a device for applying a cosmetic product. The device may include a receptacle configured to be closed so as to place the receptacle in at least a substantially sealed condition. The receptacle may include a reservoir configured to contain the cosmetic product, and an applicator for applying the cosmetic product. The applicator may be configured to be contained in the receptacle, and the device may be configured so as to permit loading of the applicator with cosmetic product from the reservoir, wherein the applicator may include a porous structure. The device may be configured such that the receptacle is configured to be unsealed from the at least substantially sealed condition so as to permit the applicator to be used for application of the cosmetic product, and to be returned to the at least substantially sealed condition with the applicator contained in the receptacle. The porous structure may include at least one biocidal agent.

As used herein, the term "cosmetic product" is defined as a make-up, treatment, and/or care product for being applied to the hair, the skin (e.g., facial skin and/or skin on any other part of the body), and/or the nails. A cosmetic product includes a product intended to be applied to any part of the body for cleansing, beautifying, promoting attractiveness, and/or altering the appearance. When the cosmetic product is (or includes) a treatment product, the treatment product may be a product sometimes used in association with, for example, losing weight, reducing wrinkles, thinning the lips and/or other tissue, moisturizing the skin (e.g., hydration creme), softening the skin, and/or reducing cellulite.

According to another aspect, the at least one biocidal agent may include one or more hydrosoluble biocidal agents. In still another aspect, the at least one biocidal agent may include one or more liposoluble biocidal agents.

Some embodiments of the invention may improve known (although not necessarily prior art) packaging and applicator devices that may use a porous structure for application purposes and/or for wiping an applicator, so as to reduce the quantity of preservative(s) contained in the substance to an amount as little as possible. Some embodiments of the invention may at least partially achieve this by virtue of the fact that the packaging and applicator device may include at least one biocidal agent incorporated in the porous structure.

According to another aspect, when the porous structure is dry, the at least one biocidal agent may be present in a solid and/or a concentrated state. In some aspects, the porous structure may be prevented from completely drying out, for example, by the receptacle being closed in an at least substantially sealed manner, and arrangements may be made to substantially ensure that the porous structure retains at least residual moisture possibly enabling the at least one biocidal agent to be activated. According to some aspects, for example, the at least one biocidal agent may be released within the porous structure, for example, to prevent it from deteriorating.

According to another aspect, the porous structure may be stressed only on its surface while the substance is being applied and/or an applicator is being wiped, and the at least one biocidal agent present in the porous structure may tend to remain contained therein and may be found in trace form only in the substance that is applied to the user, which may be advantageous, for example, when the substance is for sensitive areas. Furthermore, the porous structure may be prevented from completely drying out, which may render it possible to avoid alternating the porous structure between a dry state and a saturated and/or moist state. Such alternation may be a major factor contributing to the development of molds and/or other micro-organisms. Because the porous structure may not completely dry out, the biocidal agent may be present in a relatively small quantity.

According to yet another aspect, the porous structure may define a surface, and the porous structure may be configured to be saturated with product on the surface only. This may render it possible, for example, to substantially avoid the substance washing out the porous structure during use, and may reduce the extent to which the at least one biocidal agent passes into solution.

In a further aspect, the porous structure may include hydrophilic and lipophilic biocidal agents simultaneously.

In still another aspect, the porous structure may be at least one of hydrophilic and lipophilic, and the at least one biocidal agent may be correspondingly hydrophilic or lipophilic.

The porous structure may be hydrophilic and may render it easier for it to be completely moistened by the substance (e.g., when the substance is aqueous).

In yet a further aspect, the biocidal agent may include at least one of a bactericidal agent, a bacteriostatic agent, and an antifungal agent.

In another aspect, the biocidal agent may include metallic salts.

In yet another aspect, the porous structure may include one of a foam and a sponge. For example, the porous structure may be formed from one of polyurethane, polyester, polyether, natural rubber, synthetic rubber, butyl rubber, silicone rubber, nitrile rubber, and EPDM (e.g., a copolymer of a diene with ethylene and propylene).

According to a further aspect, the porous structure may include one of a foam and a sponge, wherein the porous structure may not be formed from any materials selected from natural rubbers and synthetic rubbers. In some examples, natural rubbers and synthetic rubbers may form compounds that develop an unpleasant odor and/or may not be hydrophilic.

According to another aspect, the porous structure may include at least 10% open cells.

In still another aspect, the porous structure may present a composite structure having, for example, a plurality of layers including different kinds (e.g. a plurality of types) of foam.

According to another aspect, a system for applying a cosmetic product may include the device for applying a cosmetic product and a cosmetic product contained in the reservoir. In some examples, the cosmetic product may contain from 0.5% to 95% water. For example, the cosmetic product may include from about 0.5% to about 95% water and/or may be a gel, and/or an emulsion, for example, an emulsion of oil in water or of water in oil.

According to a further aspect, the device (e.g., the packaging and applicator device) may be used for applying cosmetic products to skin, hair, and/or nails. For example, the cosmetic product may include a makeup product for being applied to at least one of the skin, the hair, and the nails (e.g., so as to change its/their appearance and/or scent).

According to yet another aspect, a method of conserving a porous structure may be used in the field of cosmetics products. The method may include incorporating at least one biocidal agent into a porous structure, for example, during manufacture of the porous structure, and ensuring that the porous structure does not completely dry out between uses (e.g., two uses), for example, because it is enclosed in a packaging and applicator device that may be sealed or substantially sealed.

In still another aspect, prior to moistening the porous structure, the biocidal agent may be in a solid or concentrated state, for example, at the end of manufacturing process for the porous structure, and/or while the porous structure is dry.

According to another aspect, a biocidal agent may be present in the form of crystals, for example, within the porous structure. The crystals, for example, may serve to protect the porous structure against risks of deterioration and/or they may dissolve progressively within the porous structure.

In yet another aspect, a method of manufacturing a porous structure (e.g., an open-celled porous structure) for applying a cosmetic, may include (e.g., during the process of manufacturing the porous structure) incorporating at least one biocidal agent that may be at least partially hydrosoluble into the porous structure so that the at least one biocidal agent agent returns to a solid and/or a concentrated state, for example, when the porous structure is dry.

According to a further aspect, the biocidal agent may include a composition comprising at least one quaternary ammonium compound, at least one phenolic compound, and at least one nitrogen-based heterocyclic compound. For example, the composition may comprise at least one quaternary ammonium compound, at least one isothiazolinone, and at least one orthophenylphenol. In some examples, the biocidal agent may comprise BYOTROL™.

In still another aspect, the biocidal agent may be less than about 5% by weight of the porous structure. In yet another aspect, the biocidal agent may be greater than about one and one-half percent by weight of the porous structure. For example, the biocidal agent may range from about one and one-half percent to less than about 5% by weight of the porous structure. For example, the biocidal agent may be about 3% by weight of the porous structure.

According to yet another aspect, a system may include a device and a cosmetic product contained in the reservoir of the device, wherein the porous structure includes at least one biocidal agent having a concentration by weight and the cosmetic product includes a preservative having a concentration by weight. In some examples, the concentration by weight of the biocidal agent may differ from the concentration by weight of the preservative (e.g., the biocidal concentration may be greater than the preservative concentration). For certain examples, the biocidal agent and preservative may be different from one another. Alternatively, they may be the same, or the product may have substantially no (or absolutely no) preservative at all.

In a further aspect, the device may be configured so as to permit reloading of the applicator with cosmetic product from the reservoir.

According to another aspect, the device may be configured such that when the applicator is contained in the receptacle between uses and the receptacle is placed in the at least substantially sealed condition, the porous structure may be prevented from completely drying out between uses.

In a further aspect, the receptacle may include a closure element, and the closure element may be configured to be engaged with a portion of the receptacle so as to place the receptacle in the at least substantially sealed condition.

According to another aspect, the porous structure may extend from the closure element.

In still another aspect, the receptacle may define a wall having at least one passage configured to provide flow from the reservoir to the porous structure when the closure element is engaged with a portion of the receptacle.

In still a further aspect, the porous structure may be carried by the receptacle. According to yet another aspect, the closure element and the receptacle may define a housing configured to receive the porous structure when the closure element is mounted on the receptacle.

In yet another aspect, a method of applying a cosmetic product may include providing a device for applying a cosmetic product, loading the porous structure with cosmetic product, placing the porous structure in contact with a person (e.g., in contact with skin, hair, and/or nails) so as to apply the cosmetic product, and at least substantially sealing the porous member in the receptacle such that the porous member does not dry out between uses.

In some examples, the cosmetic product may have one or more of the following exemplary features: the cosmetic product may be a product other than a make-up remover, and/or the cosmetic product may be a product other than a product intended for ophthalmic use.

According to another aspect, a device for applying a cosmetic product may include a receptacle configured to be closed so as to place the receptacle in at least a substantially sealed condition. The receptacle may include a reservoir configured to contain the cosmetic product. The device may further include an applicator for applying the cosmetic product. The applicator may include a porous structure and at least one biocidal agent. The applicator may be configured to be loaded with cosmetic product from the reservoir (e.g., at least a portion of the cosmetic product contained in the reservoir), and may be configured to be placed in contact with at least one of skin, hair, and nails so as to apply the cosmetic product. The device may be configured to permit the receptacle to be repeatedly placed in the at least substantially sealed condition with the applicator in the receptacle, and the device may be configured so as to permit reloading of the applicator with cosmetic product from the reservoir following application of the cosmetic product.

In still another aspect, a device for applying a cosmetic product may include a receptacle that may include a reservoir configured to contain the cosmetic product and an applicator for applying the cosmetic product. The applicator may include a porous structure, and the porous structure may be configured to be contained in the receptacle between uses. The porous structure may include at least one biocidal agent that may include a composition including at least one quaternary ammonium compound, at least one phenolic compound, and at least one nitrogen-based heterocyclic compound.

Aside from the structural and procedural arrangements set forth above, the invention could include a number of other arrangements, such as those explained hereinafter. It is to be understood, that both the foregoing description and the following description are exemplary.

The accompanying drawings are incorporated in and constitute a part of this specification. The drawings illustrate exemplary embodiments of the invention and, together with the description, serve to explain some principles of the invention. In the drawings, FIG. 1 is a schematic, partial cross-section view of one embodiment of a device for applying a product;

FIG. 3 is a schematic, partial cross-section view of a further embodiment of a device for applying a product;

FIG. 4 is a schematic, partial cross-section view of another embodiment of a device for applying a product;

Reference will now be made in detail to some possible embodiments of the invention, examples of which are illustrated in the accompanying drawings. Wherever possible, the same reference numbers are used in the drawings and the description to refer to the same or like parts.

Figure 1:
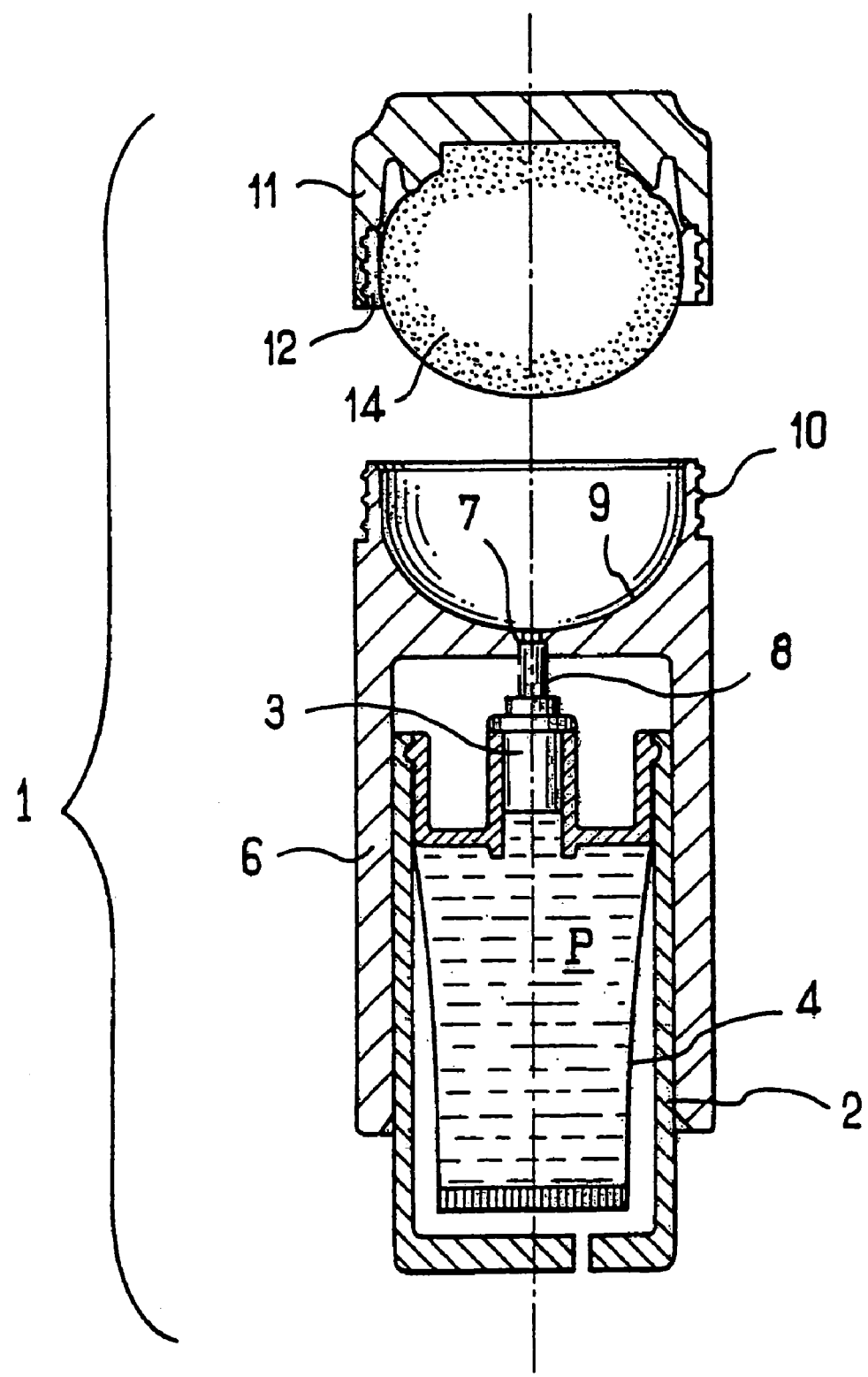

FIG. 1 depicts an exemplary embodiment of a device 1 (e.g., a packaging and/or applicator device) that includes a body 2 on which a pump 3 (e.g., an "airless" pump) is mounted. The pump 3 is configured to pump a substance P (e.g., a cosmetic product, such as an aqueous cosmetic product) contained in a reservoir 4 (e.g., a flexible bag) received in the body 2. A sliding cap 6 is mounted on the body 2. The cap 6 defines a top portion that has an externally threaded neck 10 that defines an upwardly-open housing 9 that is substantially hemispherical.

The device 1 also includes a closure cap 11 provided with an assembly skirt 12 configured to be threaded onto the threaded neck 10 so as to define a receptacle that is at least substantially sealed.

The exemplary device 1 depicted in FIG. 1 includes an applicator 14 including a porous member (e.g., a natural rubber (NRB) foam having open cells) that is fixed inside the closure element 11 and projects downwards therefrom so as to be contacted with the skin. The closure element 11 serves as a handle. The cap 6 defines an orifice passing through the bottom of the housing 9, and the orifice includes a shoulder 7 against which a rod 8 of the pump 3 bears.

The threaded neck 10 and the assembly skirt 12 are arranged to cooperate in an at least substantially sealed manner when the closure element 11 is engaged with the cap 6, thereby preventing the applicator 14 from drying out completely. In at least some examples, preventing the applicator from completely drying out may reduce the likelihood of bacteria and germs growing on the porous structure of the applicator 14. A biocidal agent is incorporated into the applicator 14.

In some examples, the biocidal agent may be in particulate and/or crystal form while the applicator 14 is dry. According to some examples, the biocidal agent may be at least partially hydrosoluble.

To illustrate a few examples, the biocidal agent may be selected from at least one of the following: salicylic acid; sodium sulfite; boric acid; sodium metabisulfite; benzoic acid; sodium benzoate; propyl p-hydroxybenzoate; methyl phydroxybenzoate; sodium methyl p-hydroxybenzoate; hydroxy-b-quinoline sulfate; tri-methylammonium myristyl bromide; sodium o-phenyl phenate; stearyl dimethyl benzylammonium chloride; sorbic acid; a (58/30/12) mixture of methyl p-hydroxybenzoate, di-potassium edetate, and hexamidine di-isoethionate; chlorhexidine hydrochloride; a (7/57/22/14) mixture of propyl, methyl, butyl, and ethyl p-hydroxybenzoates; hydrated sodium dehydroacetate; potassium sorbate; 2,4,4'-trichloro-2'-hydroxy diphenylether; chloracetamide; 1,6-di(4-amidino phenoxy) hexane di-isoethionate; a (74/17/9) mixture of methyl, ethyl, and propyl p-hydroxybenzoates; (3-chloro-1-allyl-3,5,7 triazo-1-azonium) adamante chloride; a (7612/3/17) mixture of methyl, propyl p-hydroxybenzoates, 2-bromo-2-nitro-1, 3-propanediol, hexamidine diisoethionate; a mixture of disulfide pyrithion and magnesium sulfate; urea imidazolidinyl; butyl p-hydroxybenzoate; ethyl p-hydroxybenzoate; 2-bromo-2-nitro-1,3-propanediol; sodium mercury ethyl thiosalicylate; a mixture of alkyl, dimethyl, benzyl, and ammonium chlorides; a (34/33/33) mixture of dehydroacetic acid, 2,4,4'-trichloro-2'-hydroxy-diphenylether, and propyl p-hydroxybenzoate; a (80/3/17) mixture of methyl and propyl p-hydroxybenzoates and hexamidine di-isoethionate; (2-heptyl-1-methyl-2-thiazolylidene)-2,2 methylene 3-heptyl-2-methyl thiazolynium iodide; 1-hydroxy, 4-methyl-6-trimethylpentyl-2-pyridone; monoethanolamine salts; dehydroacetic acid; iso-propyl metacresol; 2,4,6-cycloheptatrien-1-one-2-hydroxy(1-methyl-4-ethyl), N-(hydroxy-methyl) N-(1,3-di-hydroxy-methyl-di-2-oxo-4-imidazolidinyl) N-(hydroxy-methyl urea); a (7511517, 5/1/1.5) mixture of chlorphenesine, hexamedine di-isoethionate, and methyl, butyl, propyl parahydroxybenzoates; para-chloro-meta-xylenol; a (50/50) mixture of butyl p-hydroxybenzoate and 2,4,4'-trichloro-2'-hydroxy diphenyl ether; a (95/5) mixture of dimethyl dimethyl hydantoin and 3-iodo-2-propinyl carbamate; a (73.1/8.5/15/3.4) mixture of boric acid, hexamidine di-isoethionate, methyl p-hydroxybenzoate, and bronopol; (5-bromo-2-pyridyl) amino) 2-vinyl) 1-p-ethyl 2-picoliniumiodide; a (85.715/14.285) mixture of urea imidazolidinyl and hexamidine di-isoethionate; a (80/20) mixture of methyl p-hydroxybenzoate and hexamidine di-isoethionate; a (50/28/12/10) mixture of urea di-azolidinyl, methyl and propyl p-hydroxybenzoates, and hexamidine di-isoethionate; chlorphenesine; a (50/41.66/8.34) mixture of chlorphenesine, and methyl and propyl p-hydroxybenzoates; a (60/40) mixture of chlorphenesine and methyl p-hydroxybenzoate; behenyl trimethyl ammonium chloride; and sodium ethyl para-hydroxybenzoate. Other examples are possible.

Another exemplary biocidal agent includes a composition comprising at least one quaternary ammonium compound, at least one phenolic compound, and at least one nitrogen-based heterocyclic compound. One example of such a composition comprises at least one quaternary ammonium compound, at least one isothiazolinone, and at least one orthophenylphenol. In some examples, the biocidal agent may include one or more substances marketed under the name BYOTROL™. At least some forms of BYOTROL™ may include the above-mentioned exemplary composition including at least one quaternary ammonium compound, at least one isothiazolinone, and at least one orthophenylphenol. At least some forms of BYOTROL™ may be disclosed in WO 02/062142, U.S. patent application publication no. 20030031687, published Feb. 13, 2003, and U.S. patent application publication no. 20020137631, published Sep.

26, 2002, the disclosures of which are incorporated herein by reference. One exemplary BYOTROL™ biocidal agent may be BYOTROL E4L™. One or more examples of BYOTROL™ biocidal agents may have a consistency like that of oil and be capable of being diluted in water (e.g., somewhat easily).

In some embodiments, the biocidal agent may be less than about 5% by weight of the porous structure. Alternatively, the biocidal agent may be greater than about one and one-half percent by weight of the porous structure. For example, the biocidal agent may range from about one and one-half percent to less than about 5% by weight of the porous structure (e.g., the biocidal agent may be about 3% by weight of the porous structure).

In some exemplary embodiments, a system may include a device and a cosmetic product contained in the reservoir of the device, and the porous structure may include at least one biocidal agent having a concentration by weight and the cosmetic product may include a preservative having a concentration by weight. In some examples, the concentration by weight of the biocidal agent may differ from the concentration by weight of the preservative (e.g., the biocidal concentration may be greater than the preservative concentration). For certain examples, the biocidal agent and preservative may be different from one another. Alternatively, they may be the same, or the product may have substantially no (or absolutely no) preservative at all.

In addition to the biocidal agents discussed in the two preceding paragraphs, the porous structure may include at least one material selected from metallic salts of, for example, silver, copper, or ferric oxides.

In at least some examples, the biocidal agent may have one or more of the following features: the biocidal agent may be a substance that does not pollute (e.g., contaminate) the cosmetic product to be applied; the biocidal agent may be a substance that does not prevent the porous structure (e.g., foam) from exhibiting desired mechanical properties and/or porosity; the biocidal agent may kill at least substantially all bacteria and germs likely to develop after the applicator is placed in contact with the skin, hair, and/or nails (e.g., after the applicator is placed in contact with skin/hair/nails and stored for a period of time in the receptacle before its next use); the biocidal agent may be relatively inexpensive; and the efficacy of the biocidal agent may be sufficient to avoid using a high biocidal agent concentration that may be toxic to workers during manufacture of the applicator.

Figure 2:
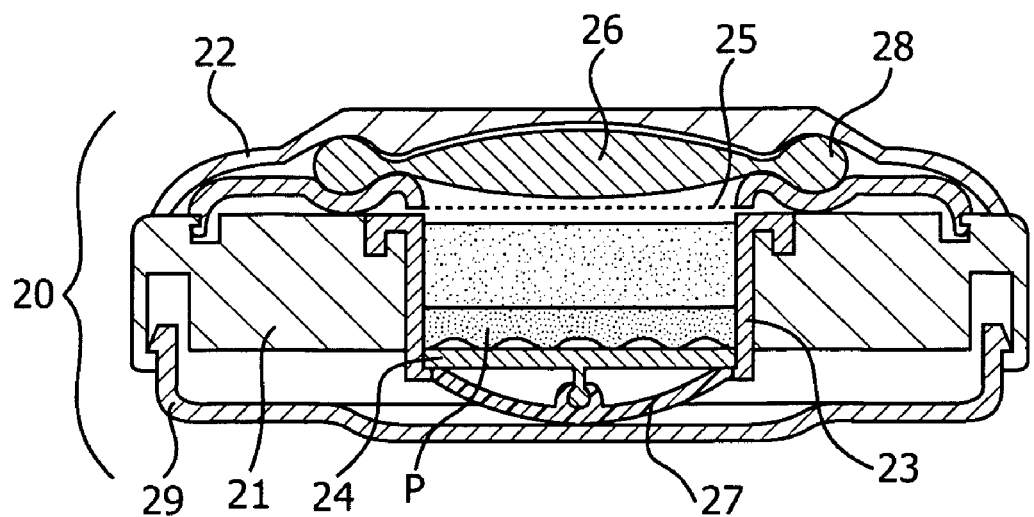
FIG. 2 is a schematic, partial cross-section view of another embodiment of a device for applying a product.

In the exemplary embodiment depicted in FIG. 2, a device 20 (e.g., a packaging and/or applicator device) includes a box having a body 21, a closure element 22 (e.g., a hinged lid), and a bottom 29 (e.g., a sliding bottom).

The body 21 includes a housing configured to receive a cup 23 defining a reservoir containing a supply of substance P. The cup 23 is provided on top with a screen 25 and underneath with a deformable wall 27. A piston 24 secured to the deformable wall 27 slides in the cup 23. By pressing against the bottom 29, the user urges the piston 24 upwards, thereby expelling substance through the screen 25.

The exemplary embodiment of device 20 depicted in FIG. 2 includes an applicator 26 constituted by a porous structure (e.g., a sponge) that may be received in the closure element 22 beyond the screen 25. The device 20 is configured to ensure that the applicator 26 is stored in at least a substantially sealed manner in the receptacle defined by the device 20. The applicator 26 is secured at its periphery to an annular rim 28 which serves as a sealing gasket by being pinched when the box is closed between the closure element 22 and a mask mounted on the body 21. The applicator 26 is thus prevented from completely drying out while the closure element 22 is closed.

The applicator 26 incorporates a biocidal agent (e.g., a biocidal agent as discussed above).

In the exemplary embodiment depicted in FIG. 3, a device 30 (e.g., a dispensing and/or packaging device) includes a receptacle portion 31 defining a product-containing reservoir and having a neck 32 that may include an outside thread. The neck 32 has a perforated wall 33 on the inside at the bottom. The device 30 includes an applicator 35 extending from (and carried by) a closure element 36 (e.g., a cap defining handle) for closing the neck 32. The applicator 35 is partially engaged with and fixed to an assembly skirt 37 of the closure element 36. The closure element and receptacle portion define a receptacle. The closure element 36 has a sealing gasket 38 shaped to fit in an at least a substantially sealed manner in the neck 32 when the closure element 36 is threaded onto the neck 32.

The applicator 35 is constituted by a porous structure (e.g., an open-celled polyurethane foam) and it incorporates a biocidal agent as described above.

In the exemplary embodiment depicted in FIG. 4, a device 50 (e.g., a dispensing and/or packaging device) may include a flexible tube 54 defining a product-containing reservoir and having a neck including an outside thread 51. The neck is fitted internally with an applicator 52 constituted by a porous structure (e.g., a block of open-celled polyether foam) that extends from the neck. The applicator 52 incorporates a biocidal agent as discussed above. When not in use, the tube 54 may be closed in at least a substantially sealed manner by a closure element 53 (e.g., a cap). The tube and closure element define a receptacle.

Figure 5:
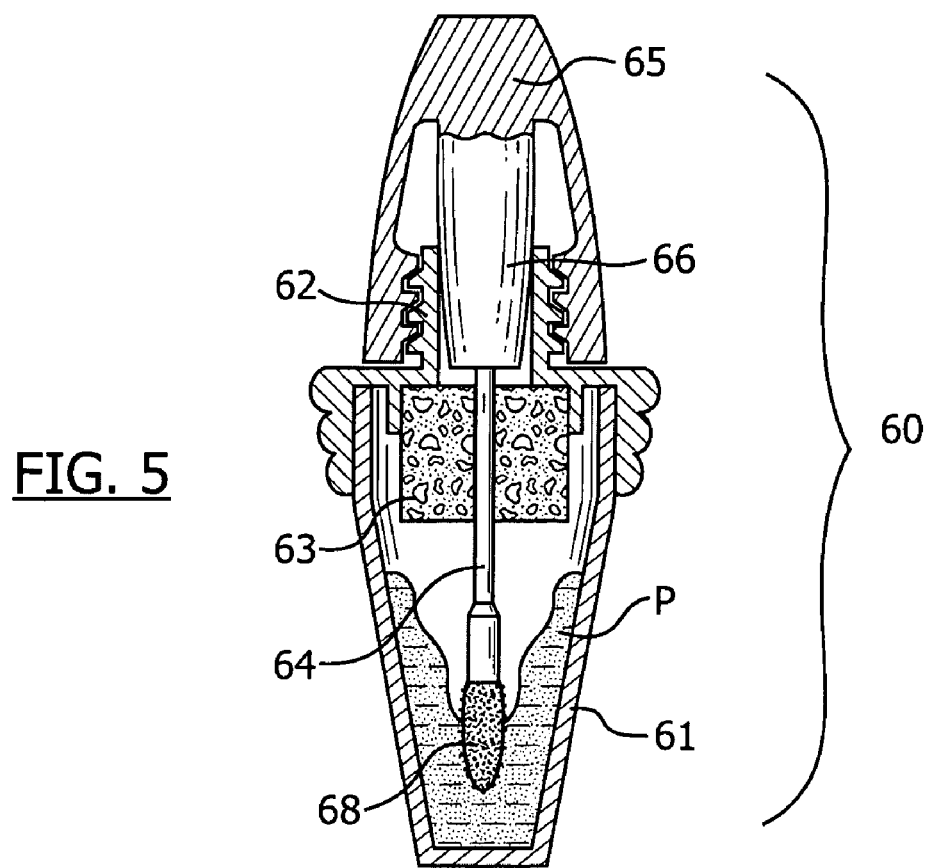
FIG. 5 is a schematic, partial cross-section view of a further embodiment of a device for applying a product.

In the exemplary embodiment depicted in FIG. 5, a device 60 (e.g., a packaging and/or applicator device) includes a receptacle portion 61 provided with a neck 62 having an outside thread. The device 60 includes a wiper member 63 constituted by a porous structure (e.g., a block of open-celled polyurethane foam) that is split axially. The wiper member 63 is fixed inside the receptacle portion 61 beneath the neck 62. The receptacle portion 61 may be closed by a closure element 65 (e.g., a cap), for example, threaded onto the neck 62. The closure element 65 includes a central portion 66 configured to fit in an at least substantially sealed manner in the neck 62. The central portion 66 extends downward via a stalk 64, which may include at its end a flocked applicator 68. The wiper member 63 serves to wipe the stalk 64 and the applicator 68 while they are being extracted from the receptacle portion 61. The porous structure of the wiper member 63 includes at least one biocidal agent as discussed above.

Figure 6:
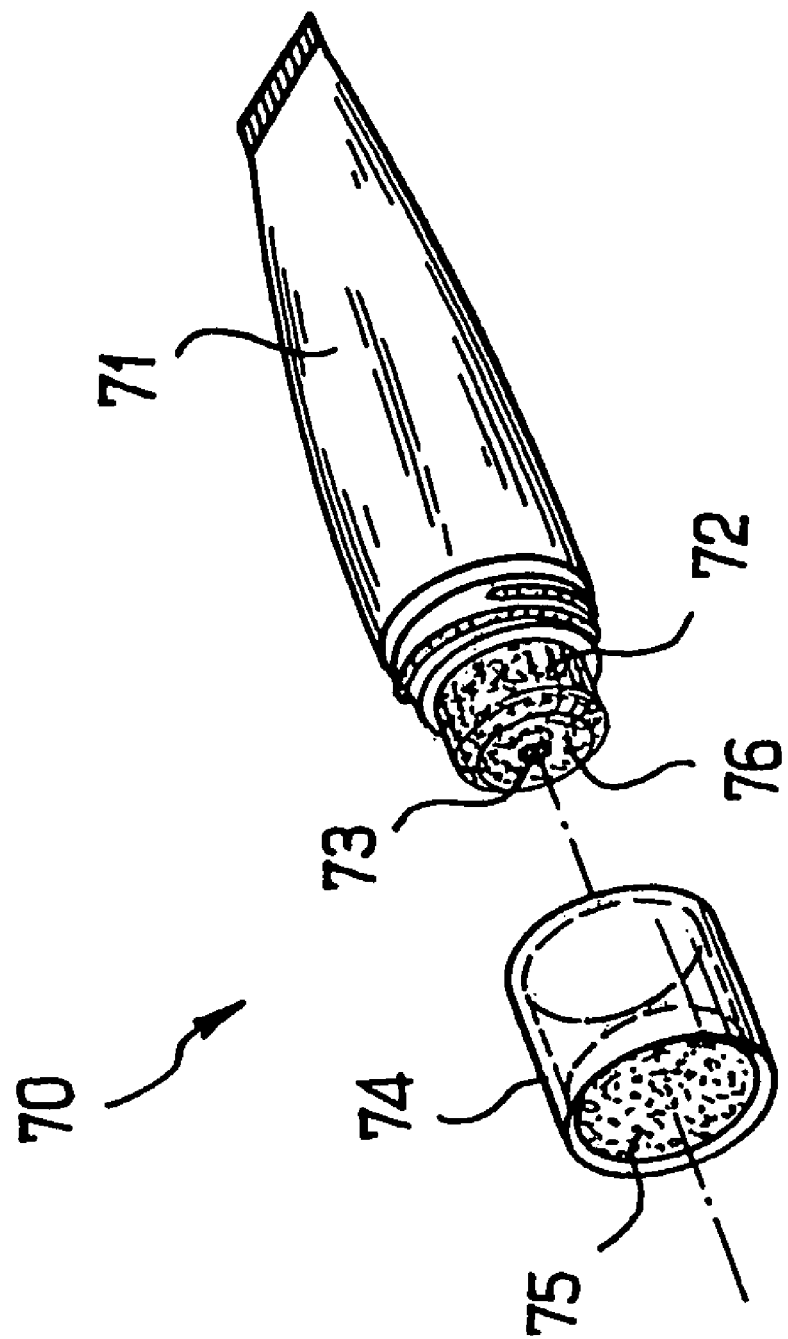
FIG. 6 is a schematic perspective view of another embodiment of a device for applying a product.

In the exemplary embodiment depicted in FIG. 6, a device 70 (e.g., a packaging and/or applicator device) includes a flexible-walled tube 71 defining a reservoir containing a cosmetic product (e.g., a makeup foundation, such as, for example, a cosmetic milk). The tube 71 is provided with an applicator 72 that is elastically deformable, and that incorporates at least one biocidal agent discussed above. An orifice 73 passes through the applicator member 72, thereby enabling the substance contained in the tube 71 to reach the surface 76 of the applicator 72 more easily in order to enable the substance to be applied on the user. The device 70 includes a closure element 74 (e.g., a cap made of a transparent plastics material). The tube 71 and closure element 74 define a receptacle. The closure element 74 may contain a supply 75 of a substance that differs from the substance contained in the tube 71. The substance contained in the closure element 74 may include a cake of colored substance configured for crumbling on contact with the substance contained in the tube 71. When the closure element 74 is mounted on the tube 71, a surface 76 of the applicator 72 bears against the supply of substance. The closure element 74 is configured to close the tube 71 in an at least substantially sealed manner when it is in mounted on the tube 71.

According to some exemplary embodiments, the applicator and/or wiper member may be conserved in a sealed or substantially sealed enclosure while the applicator and/or wiper member is not in use, such that the applicator and/or wiper member does not dry out completely and/or retains residual moisture that may serve to activate the biocidal agent(s) it contains. The applicator and/or wiper member may be substantially preserved from any deterioration due to micro-organisms. Because the porous structure (e.g., cellular material) constituting the applicator and/or wiper member may be conserved in this way, it may be possible to reduce the preservative content in the substance since the substance is not required to conserve the porous structure (e.g., cellular material), and may just contribute to activating the biocidal agent(s) contained in the applicator and/or wiper member.

A biocidal agent may be incorporated in the porous structure during manufacture (e.g., during the step of filling the plastics material (e.g., when the porous structure includes a plastics material)). The porous structure may contain at least one biocidal agent and may be used, for example, as a supply of substance by being loaded with the substance (e.g., via soaking the porous material in the substance).

According to some exemplary embodiments, the porous structure may be flocked and/or it may include a larger or smaller amount of open cells. The porous structure (e.g., cellular material) may receive hydrophilic treatment, for example, after it has been formed and/or while it is being formed via incorporating hydroabsorbers and/or fibers (e.g., polyacrylate, colloidal silica, alginates, glycerin, cotton fibers, and/or starch, this list being non-limiting).

It will be apparent to those skilled in the art that various modifications and variations can be made to the structure and methodology of the present invention. Thus, it should be understood that the invention is not limited to the examples discussed in the specification. Rather, the present invention is intended to cover modifications and variations.

What is claimed is:

1. A system for applying a cosmetic product, the system comprising:
   a device for applying a cosmetic product, the device comprising:
      a receptacle configured to be closed so as to place the receptacle in at least a substantially sealed condition, wherein the receptacle comprises a reservoir configured to contain the cosmetic product; and
      an applicator for applying the cosmetic product, wherein the applicator is configured to be contained in the receptacle,
      wherein the device is configured so as to permit loading of the applicator with cosmetic product from the reservoir,
      wherein the applicator comprises a porous structure, wherein the device is configured such that the receptacle is configured to be unsealed from the at least substantially sealed condition so as to permit the applicator to be used for application of the cosmetic product, and to be returned to the at least substantially sealed condition with the applicator contained in the receptacle, and
      wherein the porous structure comprises at least one biocidal agent, and
   a cosmetic product contained in the reservoir,
   wherein the cosmetic product comprises at least one preservative, and
   wherein a biocidal agent concentration by weight of the porous structure differs from a preservative concentration by weight of the cosmetic product.

2. The system of claim 1, wherein, prior to moistening the porous structure, the biocidal agent is in a solid or concentrated state.

3. The system of claim 1, wherein the porous structure defines a surface, the porous structure being configured to be saturated with product on the surface only.

4. The system of claim 1, wherein the porous structure is hydrophilic.

5. The system of claim 1, wherein the biocidal agent comprises at least one of a bactericidal agent, a bacteriostatic agent, and an antifungal agent.

6. The system of claim 1, wherein the biocidal agent comprises at least one hydrosoluble biocidal agent.

7. The system of claim 1, wherein the biocidal agent comprises at least one liposoluble biocidal agent.

8. The system of claim 1, wherein the biocidal agent comprises metallic salts.

9. The system of claim 1, wherein the porous structure comprises one of a foam and a sponge, the porous structure being formed from one of polyurethane, polyester, polyether, natural rubber, synthetic rubber, butyl rubber, silicone rubber, nitrile rubber, and EPDM.

10. The system of claim 9, wherein the porous structure comprises at least 10% open cells.

11. The system of claim 1, wherein the porous structure comprises one of a foam and a sponge, the porous structure not being formed from materials selected from natural rubbers and synthetic rubbers.

12. The system of claim 1, wherein the biocidal agent comprises a composition comprising at least one quaternary ammonium compound, at least one phenolic compound, and at least one nitrogen-based heterocyclic compound.

13. The system of claim 12, wherein the composition comprises at least one quaternary ammonium compound, at least one isothiazolinone, and at least one orthophenylphenol.

14. The system of claim 12, wherein the biocidal agent comprises BYOTROL.

15. The system of claim 1, wherein the biocidal agent is less than about 5% by weight of the porous structure.

16. The system of claim 1, wherein the biocidal agent is more than about one and one-half percent by weight of the porous structure.

17. The system of claim 1, wherein the biocidal agent is from less than about 5% by weight of the porous structure to more than about one and one-half percent by weight of the porous structure.

18. The system of claim 1, wherein the biocidal agent is about 3% by weight of the porous structure.

19. The system of claim 1, wherein the device is configured so as to permit reloading of the applicator with cosmetic product from the reservoir.

20. The system of claim 1, wherein the device is configured such that when the applicator is contained in the receptacle between uses and the receptacle is placed in the at least substantially sealed condition, the porous structure is prevented from completely drying out between uses.

21. The system of claim 1, wherein the receptacle further comprises a closure element, and wherein the closure element is configured to be engaged with a portion of the receptacle so as to place the receptacle in the at least substantially sealed condition.

22. The system of claim 21, wherein the porous structure extends from the closure element.

23. The system of claim 21, wherein the receptacle defines a wall having at least one passage configured to provide flow communication from the reservoir to the porous structure when the closure element is engaged with the portion of receptacle.

24. The system of claim 21, wherein the porous structure extends from the portion of the receptacle.

25. The system of claim 24, wherein the receptacle defines a housing configured to receive the porous structure when the closure element is engaged with the portion of the receptacle.

26. The system of claim 1, wherein the cosmetic product comprises a makeup product for being applied to at least one of skin, hair, and nails.

27. A system for applying a cosmetic product, the system comprising:
   a device for applying a cosmetic product, the device comprising:
      a receptacle configured to be closed so as to place the receptacle in at least a substantially sealed condition, wherein the receptacle comprises a reservoir configured to contain the cosmetic product; and
      an applicator for applying the cosmetic product, wherein the applicator is configured to be contained in the receptacle,
      wherein the device is configured so as to permit loading of the applicator with cosmetic product from the reservoir,
      wherein the applicator comprises a porous structure,
      wherein the device is configured such that the receptacle is configured to be unsealed from the at least substantially sealed condition so as to permit the applicator to be used for application of the cosmetic product, and to be returned to the at least substantially sealed condition with the applicator contained in the receptacle, and
      wherein the porous structure comprises at least one biocidal agent; and
   a cosmetic product contained in the reservoir,
   wherein the cosmetic product comprises at least one preservative and wherein the biocidal agent is different from the preservative.

28. A method of applying a cosmetic product, the method comprising
   providing the system of claim 1;
   loading the porous structure with cosmetic product;
   placing the porous structure in contact with a person so as to apply the cosmetic product; and
   at least substantially sealing the porous member in the receptacle such that the porous member does not dry out between uses.

29. A system for applying a cosmetic product, the system comprising:
   a device for applying a cosmetic product, the device comprising:
      a receptacle configured to be closed so as to place the receptacle in at least a substantially sealed condition, wherein the receptacle comprises a reservoir configured to contain the cosmetic product; and
      an applicator for applying the cosmetic product, the applicator comprising
         a porous structure, and
         at least one biocidal agent,
      wherein the applicator is configured to be loaded with cosmetic product from the reservoir,
      wherein the applicator is configured to be placed in contact with at least one of skin, hair, and nails so as to apply the cosmetic product,
      wherein the device is configured to permit the receptacle to be repeatedly placed in the at least substantially sealed condition with the applicator in the receptacle, and
      wherein the device is configured so as to permit reloading of the applicator with cosmetic product from the reservoir following application of the cosmetic product, and
   a cosmetic product contained in the reservoir,
   wherein the cosmetic product comprises at least one preservative, and
   wherein a biocidal agent concentration by weight of the porous structure differs from a preservative concentration by weight of the cosmetic product.

30. The system of claim 29, wherein the at least one biocidal agent comprises a composition comprising at least one quaternary ammonium compound, at least one phenolic compound, and at least one nitrogen-based heterocyclic compound.

31. The system of claim 30, wherein the composition comprises at least one quaternary ammonium compound, at least one isothiazolinone, and at least one orthophenylphenol.

32. The system of claim 29, wherein the at least one biocidal agent comprises BYOTROL.

33. The system of claim 29, wherein the biocidal agent is less than about 5% by weight of the porous structure.

34. The system of claim 29, wherein the biocidal agent is more than about one and one-half percent by weight of the porous structure.

35. The system of claim 29, wherein the biocidal agent is from less than about 5% by weight of the porous structure to more than about one and one-half percent by weight of the porous structure.

36. The system of claim 29, wherein the at least one biocidal agent is about 3% by weight of the porous structure.

37. A method of applying a cosmetic product, the method comprising
   providing the system of claim 29;
   loading the porous structure with cosmetic product;
   placing the porous structure in contact with a person so as to apply the cosmetic product; and
   at least substantially sealing the porous member in the receptacle such that the porous member does not dry out between uses.

38. A device for applying a cosmetic product, the device comprising:
   a receptacle comprising a reservoir configured to contain the cosmetic product;
   an applicator for applying the cosmetic product, the applicator comprising a porous structure, the porous structure being configured to be contained in the receptacle between uses, wherein the porous structure comprises at least one biocidal agent comprising a composition comprising at least one quaternary ammonium compound, at least one phenolic compound, and at least one nitrogen-based heterocyclic compound.

39. The device of claim 38, wherein the composition comprises at least one quaternary ammonium compound, at least one isothiazolinone, and at least one orthophenylphenol.

40. The device of claim 38, wherein the at least one biocidal agent comprises BYOTROL.

41. The device of claim 38, wherein the biocidal agent is less than about 5% by weight of the porous structure.

42. The device of claim 38, wherein the biocidal agent is more than about one and one-half percent by weight of the porous structure.

43. The device of claim 38, wherein the biocidal agent is from less than about 5% by weight of the porous structure to more than about one and one-half percent by weight of the porous structure.

44. The device of claim 38, wherein the at least one biocidal agent is about 3% by weight of the porous structure.

45. The system of claim 1, wherein the porous structure is formed from polyester.

46. The system of claim 1, wherein the porous structure is formed from polyether.

47. The system of claim 1, wherein the biocidal agent concentration by weight of the porous structure is greater than the preservative concentration by weight of the cosmetic product.

* * * * *